US012413264B2

(12) United States Patent
Steffens

(10) Patent No.: US 12,413,264 B2
(45) Date of Patent: Sep. 9, 2025

(54) HIGH DENSITY ROTARY JOINT FOR CONTACTLESS DATA TRANSFER

(71) Applicant: Schleifring GmbH, Fürstenfeldbruck (DE)

(72) Inventor: Holger Steffens, Munich (DE)

(73) Assignee: Schleifring GmbH, Fürstenfeldbruck (DE)

( * ) Notice: Subject to any disclaimer, the term of this patent is extended or adjusted under 35 U.S.C. 154(b) by 0 days.

(21) Appl. No.: 19/051,994

(22) Filed: Feb. 12, 2025

(65) Prior Publication Data

US 2025/0233617 A1   Jul. 17, 2025

Related U.S. Application Data

(63) Continuation of application No. PCT/EP2023/054185, filed on Feb. 20, 2023.

(30) Foreign Application Priority Data

Aug. 19, 2022   (EP) .................................. 22191190.2

(51) Int. Cl.
*H04B 5/00* (2024.01)
*G02F 1/225* (2006.01)
(Continued)

(52) U.S. Cl.
CPC ...................... *H04B 5/22* (2024.01)

(58) Field of Classification Search
None
See application file for complete search history.

(56) References Cited

U.S. PATENT DOCUMENTS 5,892,411 A * 4/1999 Schwan .................. H04B 5/00
333/32
6,420,842 B1 * 7/2002 Gold ....................... H02H 7/06
318/141

(Continued)

FOREIGN PATENT DOCUMENTS

EP    1867073 B1   5/2013
EP    2775630 A1   9/2014
EP    2932901 A1   10/2015

OTHER PUBLICATIONS

European Patent Office, Extended Search Report, Application No. 22191190.2, Dec. 22, 2022, 11 pages.

(Continued)

*Primary Examiner* — Tuan A Tran
(74) *Attorney, Agent, or Firm* — Quarles & Brady LLP; Yakov Sidorin

(57) ABSTRACT

A rotating capacitive data link system includes a first body rotatable relative to a second body. The first body has one or multiple circular signal transmission lines with multiple transmission line segments. The second body has multiple circular arranged sets of receiving couplers with multiple receiving couplers. Each of the sets of receiving couplers matches to one of the circular signal transmission lines, such that depending on the relative rotational position or angle between the first body and the second body multiple capacitively coupled paths between the transmission line segments and the receiving couplers of a matching set of receiving couplers exist. A receive signal processor is provided to generate a detailed error or status matrix of transmission errors.

12 Claims, 12 Drawing Sheets

(51) Int. Cl.
  *H01L 41/22* (2013.01)
  *H04B 5/02* (2006.01)
  *H04B 5/22* (2024.01)
  *H04L 7/00* (2006.01)

(56) References Cited

U.S. PATENT DOCUMENTS

| | | | | |
|---|---|---|---|---|
| 7,240,251 | B2* | 7/2007 | Popescu | H04L 1/24 |
| | | | | 714/704 |
| 7,423,257 | B2* | 9/2008 | Popescu | A61B 6/035 |
| | | | | 250/227.14 |
| 7,466,794 | B2 | 12/2008 | Krumme | |
| 7,663,462 | B2* | 2/2010 | Makuth | H01F 38/18 |
| | | | | 336/130 |
| 8,013,468 | B2 | 9/2011 | Lohr | |
| 8,126,298 | B2* | 2/2012 | Stark | G08C 17/06 |
| | | | | 385/26 |
| 8,369,780 | B2* | 2/2013 | Bauer | H04B 5/00 |
| | | | | 307/104 |
| 8,594,480 | B2* | 11/2013 | Krumme | A61B 6/56 |
| | | | | 378/19 |
| 8,731,348 | B2* | 5/2014 | Krumme | H01G 5/01 |
| | | | | 378/4 |
| 9,312,925 | B2* | 4/2016 | Kusaka | H04B 5/79 |
| 9,342,398 | B2 | 5/2016 | Li et al. | |
| 9,757,089 | B2* | 9/2017 | Reichel | A61B 6/03 |
| 9,859,994 | B2* | 1/2018 | Steffens | H04B 5/72 |
| 9,974,513 | B2* | 5/2018 | Hannemann | A61B 6/035 |
| 10,033,074 | B2* | 7/2018 | Coleman | H01P 1/062 |
| 10,079,090 | B2* | 9/2018 | Teggatz | H01F 38/14 |
| 10,222,200 | B2* | 3/2019 | Hatcher, Jr. | G01B 11/14 |
| 10,483,805 | B2* | 11/2019 | Kahlman | H04B 5/26 |
| 10,984,947 | B2* | 4/2021 | Grünberg | H04B 5/79 |
| 11,349,527 | B2* | 5/2022 | Kirby | H04B 5/22 |
| 11,528,057 | B2* | 12/2022 | Eguchi | H04B 5/72 |
| 11,722,180 | B2* | 8/2023 | Eguchi | H04L 7/0008 |
| | | | | 455/41.1 |
| 11,736,145 | B2* | 8/2023 | Pearson, Jr. | H01Q 9/285 |
| | | | | 455/41.1 |
| 2005/0005206 | A1 | 1/2005 | Popescu | |
| 2008/0069146 | A1 | 3/2008 | Krumme | |
| 2018/0241250 | A1* | 8/2018 | Kahlman | H04B 5/22 |
| 2020/0373641 | A1* | 11/2020 | Krumme | G02B 6/3604 |

OTHER PUBLICATIONS

PCT International Search Report and Written Opinion, PCT/EP2023/054185, Mar. 20, 2023, 18 pages.

* cited by examiner

FIG. 1 (sub-Fig. 1a)
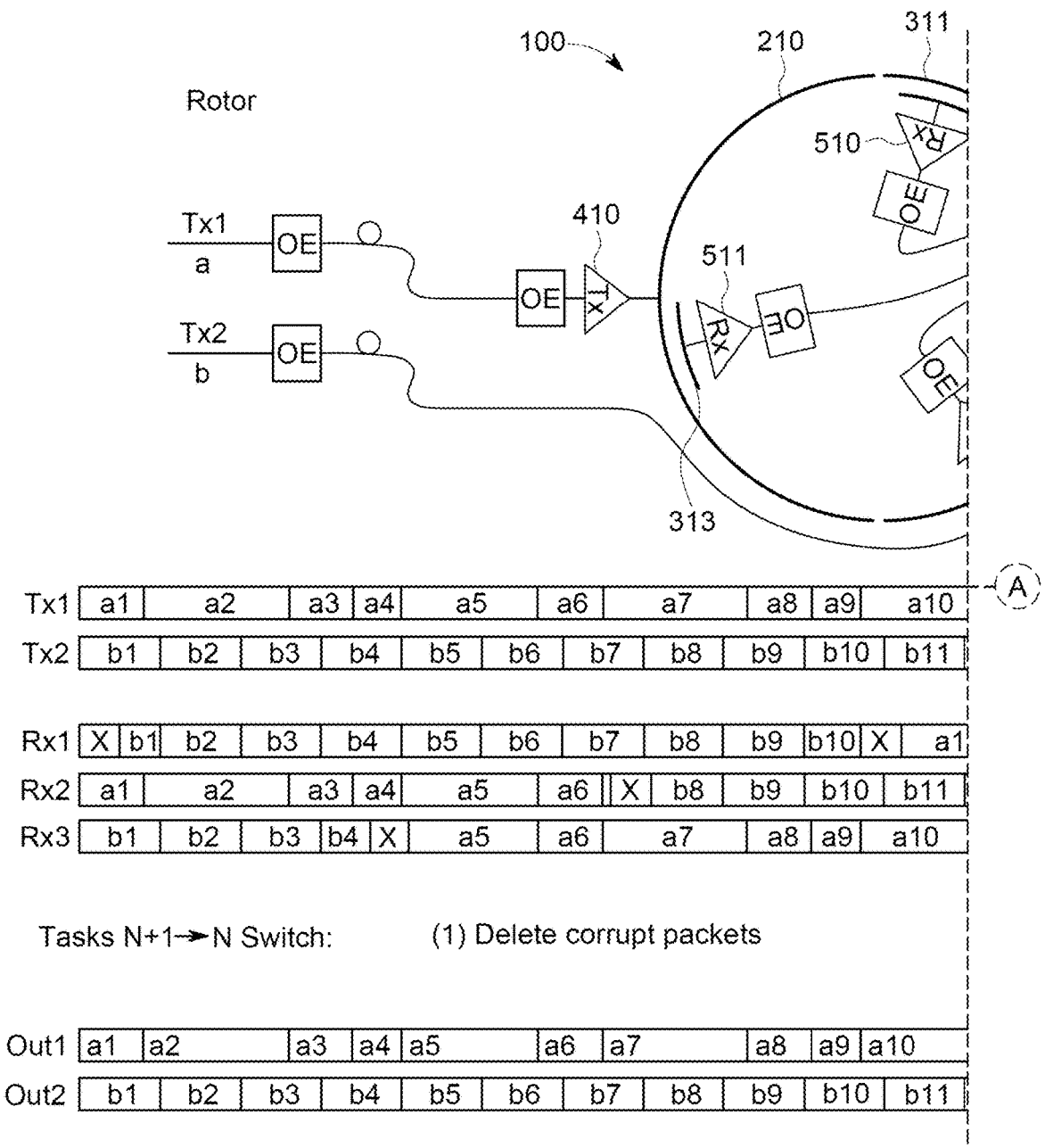

FIG. 1 (continued; sub-Fig. 1b)
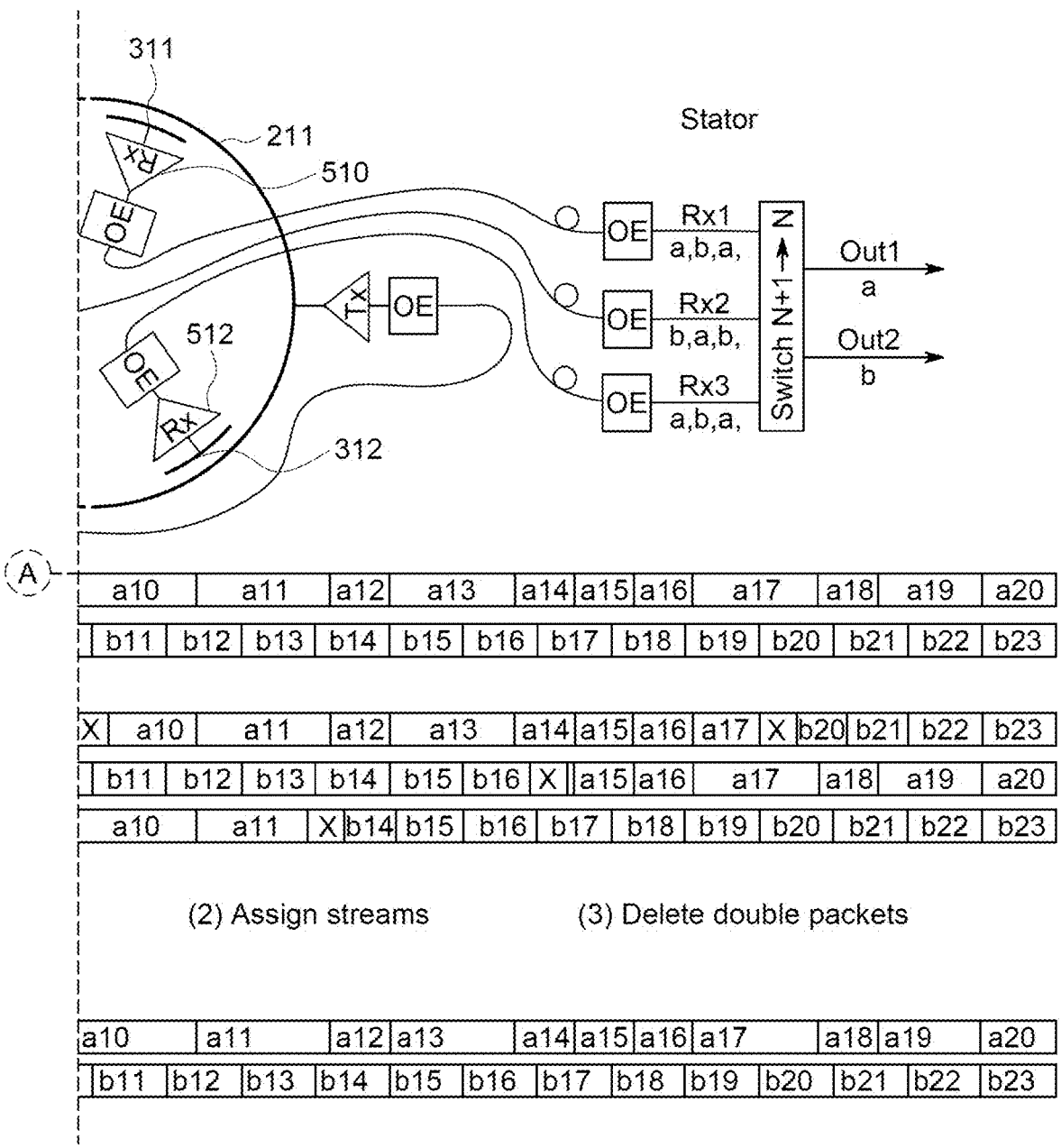

FIG. 4 (sub-Fig. 4a)
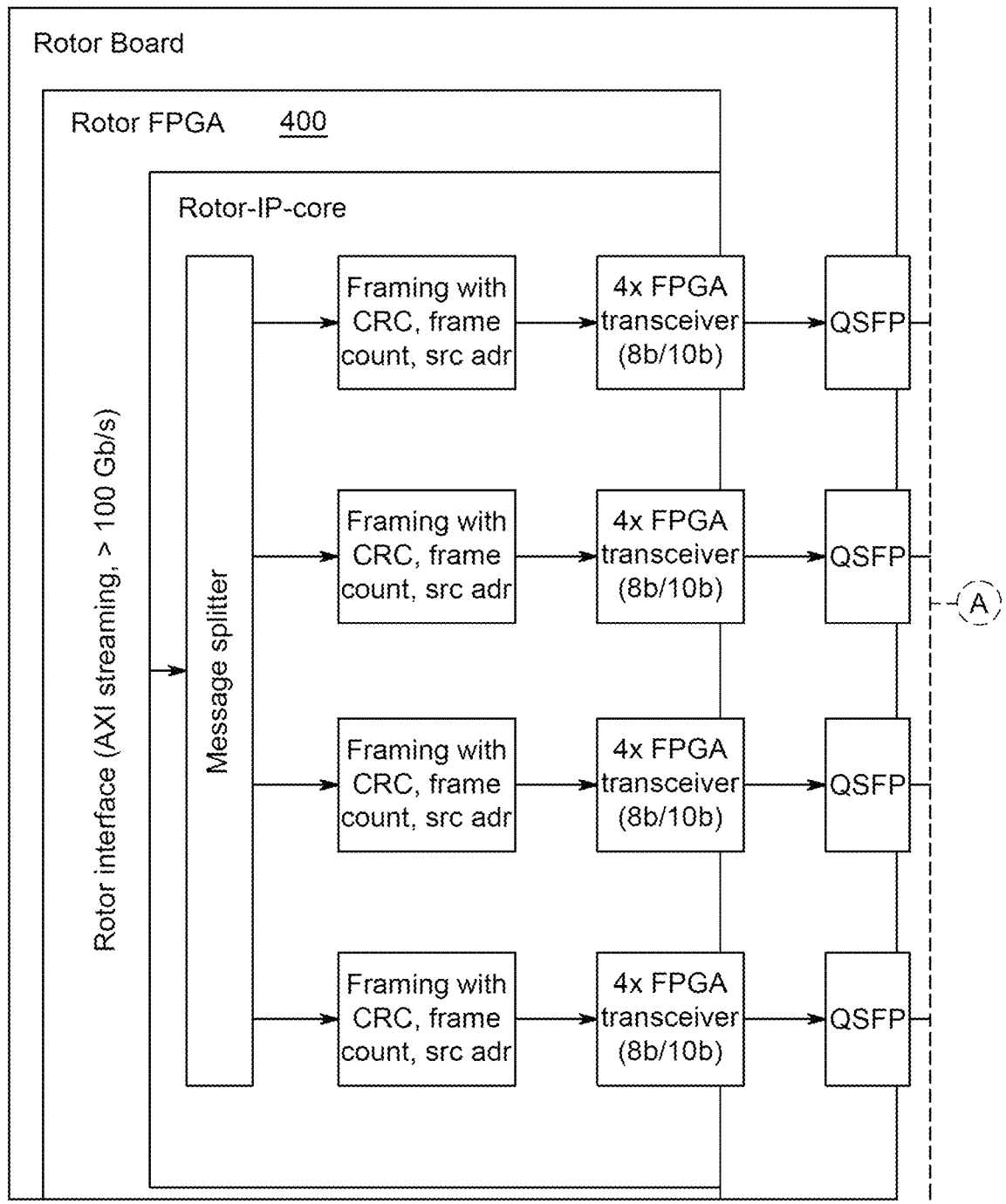

FIG. 4 (continued; sub-Fig. 4b)
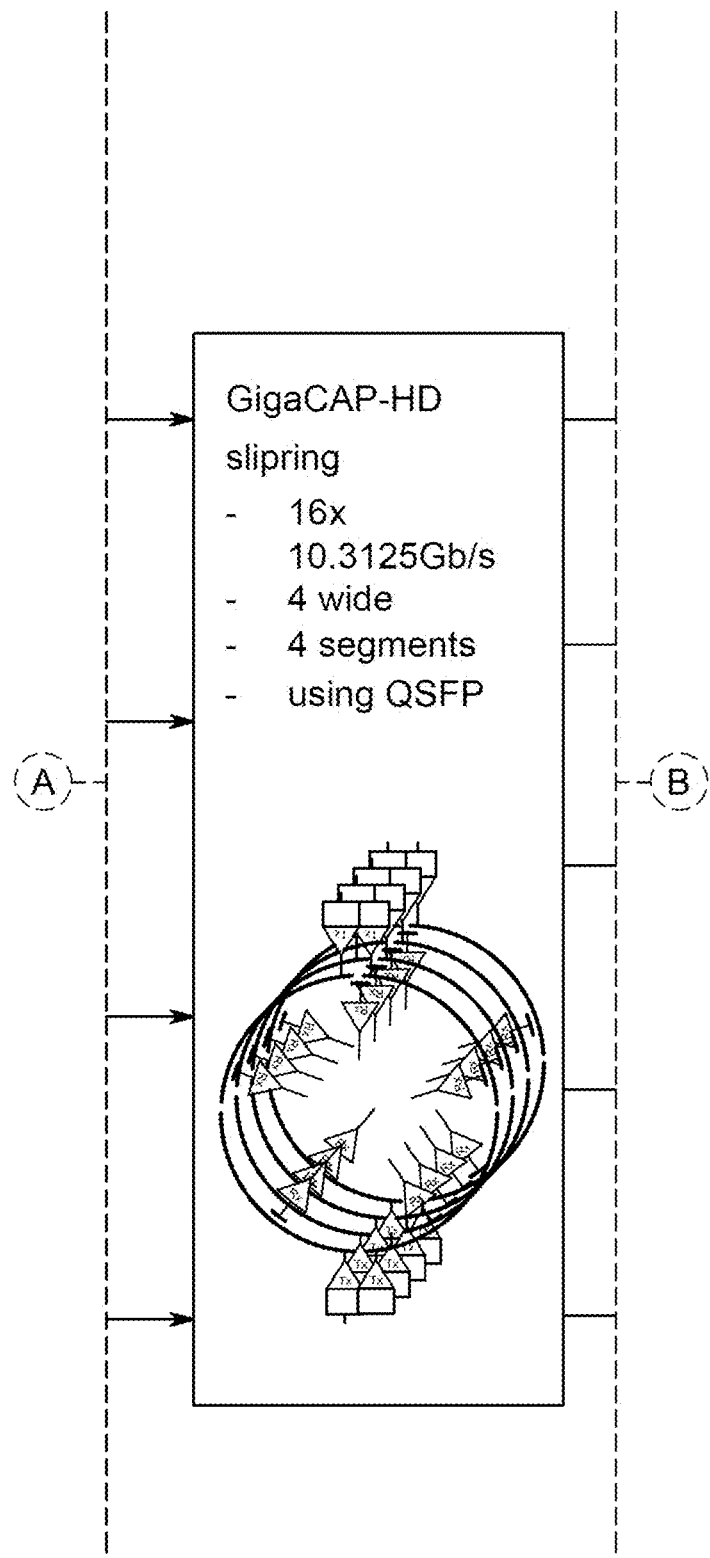

FIG. 4 (continued; sub-Fig. 4c)
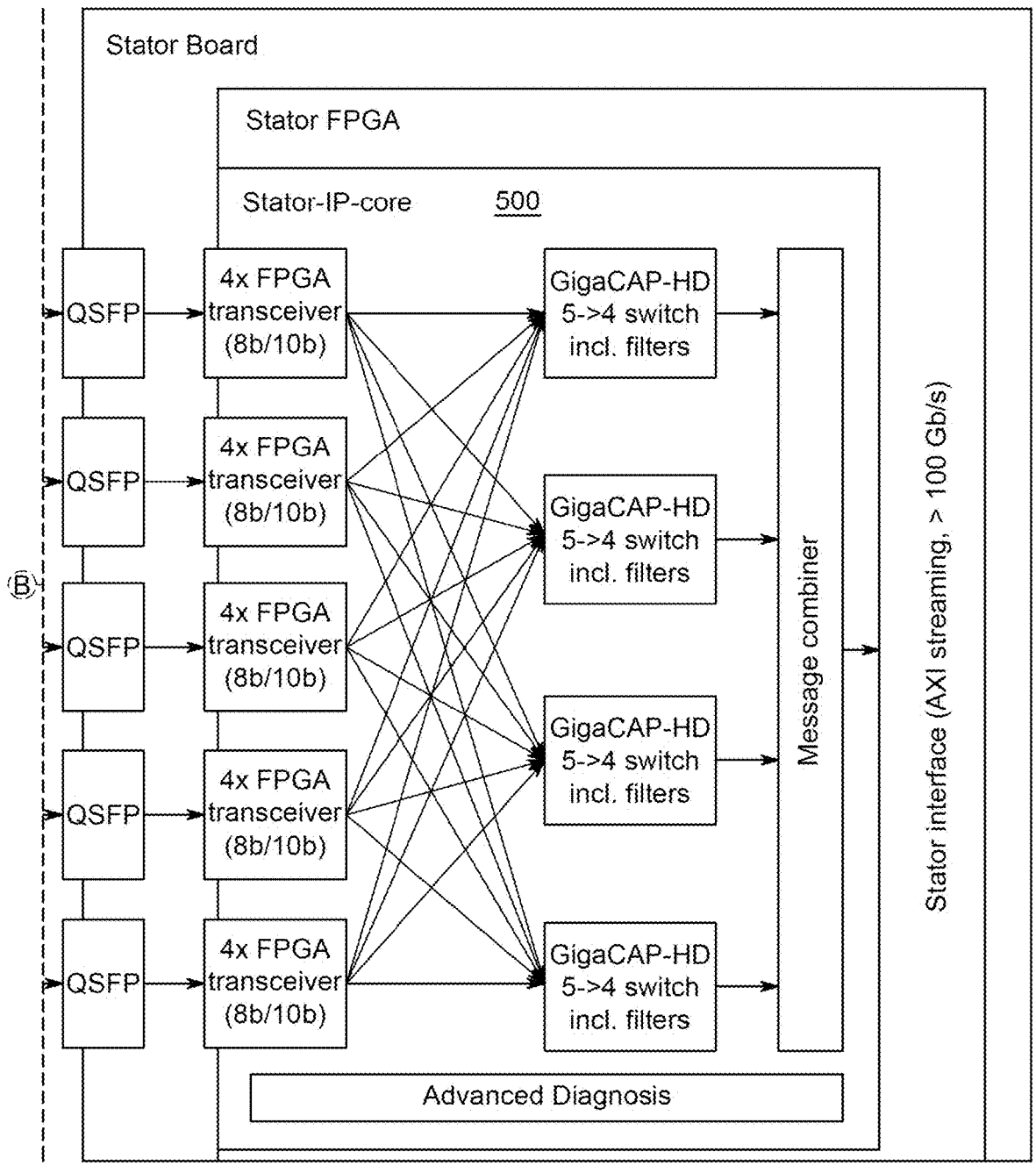

FIG. 8

| frame gap counts | TX0 | TX1 | TX2 | TX3 |
|---|---|---|---|---|
| RX0 | FG [0, 0] = 0 | FG [0, 1] = 0 | FG [0, 2] = 0 | FG [0, 3] = 0 |
| RX1 | FG [1, 0] = 0 | FG [1, 1] = 0 | FG [1, 2] = 0 | FG [1, 3] = 0 |
| RX2 | FG [2, 0] = 1 | FG [2, 1] = 3 | FG [2, 2] = 1 | FG [2, 3] = 1 |
| RX3 | FG [3, 0] = 0 | FG [3, 1] = 0 | FG [3, 2] = 0 | FG [3, 3] = 0 |
| RX4 | FG [4, 0] = 0 | FG [4, 1] = 0 | FG [4, 2] = 0 | FG [4, 3] = 0 |

910

HIGH DENSITY ROTARY JOINT FOR CONTACTLESS DATA TRANSFER

CROSS-REFERENCE TO RELATED APPLICATIONS

This US Patent application is a continuation of the pending International Application No. PCT/EP2023/054185 filed on Feb. 20, 2023 and now published as WO 2024/03744, which designates the United States and claims priority from the European Application No. 22191190.2 filed on Aug. 19, 2022. The disclosure of each of the above-identified patent documents is incorporated herein by reference.

FIELD OF THE INVENTION

The invention relates to a rotary joint for contactless data transfer based on capacitive coupling technology. To obtain very high data rates with very low data losses, multiple capacitive links are combined with a rotation angle dependent multiplexing scheme. This allows higher data transmission bandwidth while maintaining existing dimensions of the slipring system. The added complexity requires intelligent system diagnosis. Such a rotary joint may be used in a CT scanner.

RELATED ART

A multi-channel data transmission system for computer tomographs is disclosed in U.S. Pat. No. 7,466,794, which is further improved by EP 2932901. To improve transmission reliability. Existing diagnosis as described in U.S. Pat. No. 8,013,468 B2 and U.S. Pat. No. 7,240,251B2 help to find single errors in single transmission link but are of limited benefit in these complex systems that may have 36 or more data transmitter and receiver components that generate 16 parallel multiplexed data transmission links with rapidly and cyclically interchanging communication devices that may cause not only static but also dynamic errors when misaligned or defective.

US 2008/0069146 A1 discloses a multi-channel data transmission system for computer tomographs. EP 2 775 630 A1 discloses a high-speed network contactless rotary joint. US 2005/0005206 A1 discloses a method and system for data transmission in a CT device, with integrated error monitoring and diagnosis. EP 2 932 901 A1 discloses a rotary joint for multi-channel high-speed data transmission.

SUMMARY OF THE INVENTION

The problem to be solved by the invention is to provide an improved capacitive data link system with very high data rates, very low data losses and a high reliability by allowing simple diagnostics showing misalignment of data transmission components precisely and helping to find defective components fast and targeted, avoiding try and error strategy when servicing such a device. Further, the data link diagnosis features should not add to the space requirement, such that the system may fit into space available in CT scanners. Further, the system should ease commissioning and service of such a multiplexed capacitive data transmission system.

Solutions of the problem are described in the independent claims. The dependent claims relate to further improvements of the invention.

A rotating capacitive data link system includes a first body and a second body, wherein the first body is rotatable relative to the second body around a rotation axis. This includes that the first body may be stationary, and the second body is rotatable and otherwise. Further, both bodies may rotate with different speeds.

The first body includes at least one circular signal transmission lines whereby each circular transmission line includes at least two transmission line segments each segment connected to a transmitter. The segments may be separated by at least one small mechanical gap. Such gaps may be gaps in a substrate holding individual transmission line conductors or gaps between individual transmission line conductors. There may be a higher number of transmission lines and/or transmission line segments, which may help to increase data rate and to improve transmission quality. The transmission line segments may all have the same length. The number of transmission line segments may be identical for all circular transmission lines but in a different setup may vary between the transmission lines. Also, a multiplexed capacitive data transmission system and a standard (spatially unmultiplexed) capacitive data transmission system might be combined e.g., the standard system used for an uplink (stator to rotor or second to first body) with a different total data rate than the downlink multiplexed capacitive data transmission system (rotor to stator or first to second body).

The second body includes at least two circular arranged sets of receiving couplers, wherein each circular arranged sets of receiving couplers includes at least two receiving couplers arranged circumferentially around the rotation axis. Each of the sets of receiving couplers matches to one of the circular signal transmission lines plus one more receiving coupler, with that configuration it is made sure that always at least one receiver picks up the signal of one transmission line segment so that no data is lost. Each receiving coupler is connected to one receiver.

Typically for high data rate applications is that a single or multiple circular transmission lines are arranged in transmission line segments covering only a fraction (e.g. a quarter) of the circumference, each segment is transmitting one data stream. The signal is picked up by the one more receiving couplers each connected to one receiver (e.g. 5), thus ensuring that no data is lost or distorted during the relative movement of each receiver when its receiving coupler is moving by rotation between two transmission line segments. When a receiver is rotating between one segment and the next there is a gap of data transmission caused by signal distortion and signal loss which is caused by the small mechanical gap and the signal change between the two transmission line segments which are connected to different transmitters. In the following the phase when the data received by the receiver is corrupt or the frame not evaluable is called frame gap. This frame gap has a certain length in time dependent on the mechanical alignment of the receiving coupler to the transmission line segments involved, the mechanical gap between the segments, the rotational speed, the dimension of the receive antenna, the characteristic of the receiver's PLL (phased locked loop), the data rate, the frame size plus a digital synchronization time needed to detect and synchronize on the unscrambled parts of the frame. The frame gap might be larger than usual in case of a defective receiver. A multiplexer may sort out corrupt and double data frames, it may also sort the transmission frames according a transmit address within the frame header.

In a different setup the number of transmission line segments could be one higher than the number of receivers allowing the same kind of data handling and diagnosis with the only disadvantage that the data sent by the one additional transmitter has to be generated in a complex algorithm so that no data is lost during rotation.

Also, the transmit side (transmit signal processor) may encode and repackage the data stream, inserting a frame including an address to allow resorting and transmit channel related diagnosis, a checksum to check the data packages for transmission errors and other distortions. Also, the data may be encoded inserting additional information for later Forward Error Correction (FEC). In addition, the data might be scrambled with a pseudorandom bit sequence (PRBS) code to lower unwanted radiation to values well below EMC limits during transmission of the data. The frame including header and data used for the sorting or for the diagnosis or quality of the data in the following is called SR-Frame, but it can be any kind of frame, an additionally inserted frame, a user defined protocol frame or a standardized protocol frame, e.g. Ethernet or IO-Link frame if all the necessary information is included as described above.

There is a transmit signal processor at the first body and a receive signal processor at the second body. Each of the transmission line segments is connected to the transmit signal processor at the first body and each of the receiving couplers is connected to the receive signal processor at the second body. This allows a downlink data communication from the transmit signal processor at the first body via the transmission line segments and the receiving couplers to the receive signal processor at the second body. The transmit signal processor may include a plurality of transmitters connected to the transmission line segments. An individual transmitter may be connected to each of the transmission line segments. The receive signal processor may include a plurality of receivers connected to the receiving couplers. An individual receiver may be connected to each of the receiving couplers. The transmit signal processor and/or the receive signal processor may include or be a part of a FPGA and/or a microcontroller.

Depending on the relative rotational position or angle between the first body and the second body there exist multiple capacitively coupled paths between transmission line segments of each circular signal transmission line and matching receiving couplers. One high speed data stream of a user channel may be translated by a transmit signal processor to a plurality of low-speed data streams which are transferred over the multiple capacitively coupled paths, and which are assembled back to at least one high speed data stream of a user channel in a receive signal processor. Alternatively, already existing parallel data streams are transmitted in parallel links or several data streams, Ethernet frames or other protocols like slower control busses and other signals (e.g., IO-Link, CAN Bus, Encoder data, other HW Trigger signals etc.) can also be multiplexed together contributing to the data stream. If data and signals are multiplexed on the rotor of a system, they are demultiplexed on the stator (downlink) and vice versa in case of an uplink configuration. An uplink may be provided and may include an uplink receiver at the first body matching to an uplink transmitter of the second body. This allows a data communication in the opposite direction from the second body to the first body. The uplink transmitter may include at least one signal circular transmission line with at least one signal transmission line segment. The uplink receiver may include at least one receiving coupler. The uplink may be based on any suitable transmission technology, including a slipring, a capacitive datalink, an inductive datalink, an optical rotary joint. The uplink may also include of one or of several parallel data links.

Uplink and downlink may have different aggregated data transmission capacity. Normally, the uplink is only for signaling and communication protocols, such that is has a lower data rate than the downlink.

The receive signal processor is further configured to provide at least one detailed error or status matrix which may further be used for field service support. Such an error or status matrix may be provided in real-time. Generally, the embodiments relate to a matrix which may show errors or status of a data link system. Generally an error may be considered as a specific status. The status matrix may include:
  status information, e.g., values or counts,
  error information about errors, e.g., values or counts,
  information about error-free transmissions, e.g., values or counts,
  or all of the above.

Herein the terms "status matrix", "error matrix" and "error or status matrix" are used for such a matrix.

The error or status matrix includes at least one data field for every usable or matching combination of transmission line segments and receiving couplers. In an embodiment of a two-dimensional matrix, the error or status matrix has one row for every transmission line segment and a column for every receiving coupler. The matrix may have more dimensions, which may e.g., cover data rates, data formats, operating conditions like temperature or voltages. In the above two-dimensional matrix only the data fields of valid or usable/matching combinations of transmission line segments and receiving couplers may be occupied. All other data fields may be marked as invalid. There may be a single error or status matrix for the whole rotating capacitive data link system or an individual matrix for each combination of transmission line segments and receiving couplers. The error or status matrix for uplink and downlink may be separate or united in one multidimensional matrix. The setup and content of the error or status matrix may be read, evaluated, stored and displayed by a controller, e.g., by a service PC by reading and modifying registers of the transmit, receive and transceiver signal processors. The connection between controller and processors may be realized via a data link that is part of the data link system that is controlled. For redundancy in case of failures this connection may be signaled through different paths.

An example of such a matrix is given below, where the first body includes two circular signal transmission lines, each including 3 segments (each segment driven by one transmitter connected to one data link) and the second body includes two sets of receiving couplers, each including two couplers.

Since the position of the component transmitter and connected transmit segment and receiving coupler and connected receiver is defined by the wiring a wrong wiring can be detected, e.g., if the line and couplers do not fit together. This shown as error but also might be ignored by the diagnostic system if the error is not leading to a functional error, e.g., if the frames are sorted out correctly.

|  | set 1 coupler 1 | set 1 coupler 2 | set 2 coupler 1 | set 2 coupler 2 |
| --- | --- | --- | --- | --- |
| line 1 segment 1 | E(11, 11) | E(11, 12) | invalid | invalid |
| line 1 segment 2 | E(12, 11) | E(12, 12) | invalid | invalid |
| line 1 segment 3 | E(13, 11) | E(13, 12) | invalid | invalid |
| line 2 segment 1 | invalid | invalid | E(21, 21) | E(21, 22) |

-continued

|  | set 1 coupler 1 | set 1 coupler 2 | set 2 coupler 1 | set 2 coupler 2 |
|---|---|---|---|---|
| line 2 segment 2 | invalid | invalid | E(22, 21) | E(22, 22) |
| line 2 segment 3 | invalid | invalid | E(23, 21) | E(23, 23) |

Line 1 matches with set 1 and line 2 matches with set 2. Only matching pairs can communicate with each other. Therefore, only combinations of line 1 and set 1 as well as line 2 and set 2 may contain valid error counter values. The data fields of all other combinations are marked as invalid. The data fields marked with E(xx,yy) may contain certain error values. For example, E(13,12) may contain an error counter for errors from transmission of signals from line 1, segment 3 to coupler 2 of set 1. Here, the first digit x of E(xx,yy) is the line number, the second digit x is the segment. The first digit y is the set, and the second digit y is the coupler number.

The error or status matrix may contain flags or counters of errors, like code errors (e.g., no 8b10b encoding detected), frame errors as e.g. CRC errors, signal loss or it may indicate the status or availability of individual combinations of transmission line segments and receiving couplers. A CRC error is detected, and a CRC counter may be incremented if the CRC value contained within the frame is not consistent with the calculated CRC value of the frame.

The error or status matrix might also be filled with status information showing status information or calculated fitness information which is calculated from error counter values implemented as a status matrix, showing which signals are valid or connected. For ease of description only the error or status matrix is described.

An error detected will increment a counter assigned to the transmit side (transmitter connected to transmit segment) and receive side of the channel, thus allowing later a correlation of the errors, e.g., an error count is distributed over all transmit channels but only one receive channel (receiver and connected receiving coupler) shows that it is correlated with the receive channel.

Below is an error or status matrix of a perfect working data link system, where the data fields contain for example coding errors per second:

|  | set 1 coupler 1 | set 1 coupler 2 | set 2 coupler 1 | set 2 coupler 2 |
|---|---|---|---|---|
| line 1 segment 1 | 0 | 0 | invalid | invalid |
| line 1 segment 2 | 0 | 0 | invalid | invalid |
| line 1 segment 3 | 0 | 0 | invalid | invalid |
| line 2 segment 1 | invalid | invalid | 0 | 0 |
| line 2 segment 2 | invalid | invalid | 0 | 0 |
| line 2 segment 3 | invalid | invalid | 0 | 0 |

Here, all valid combination of transmission line segments and receiving couplers have zero coding errors per second.

If, for example segment 2 of line 1 is slightly misaligned, the error rate may increase for all combinations with that segment:

|  | set 1 coupler 1 | set 1 coupler 2 | set 2 coupler 1 | set 2 coupler 2 |
|---|---|---|---|---|
| line 1 segment 1 | 0 | 0 | invalid | invalid |
| line 1 segment 2 | 25325 | 35125 | invalid | invalid |
| line 1 segment 3 | 0 | 0 | invalid | invalid |
| line 2 segment 1 | invalid | invalid | 0 | 0 |
| line 2 segment 2 | invalid | invalid | 0 | 0 |
| line 2 segment 3 | invalid | invalid | 0 | 0 |

If, for example coupler 1 of set 2 is slightly misaligned, the error rate may increase for all combinations with that coupler, leading to a higher error count per measurement time:

|  | set 1 coupler 1 | set 1 coupler 2 | set 2 coupler 1 | set 2 coupler 2 |
|---|---|---|---|---|
| line 1 segment 1 | 0 | 0 | invalid | invalid |
| line 1 segment 2 | 0 | 0 | invalid | invalid |
| line 1 segment 3 | 0 | 0 | invalid | invalid |
| line 2 segment 1 | invalid | invalid | 85354 | 0 |
| line 2 segment 2 | invalid | invalid | 52145 | 0 |
| line 2 segment 3 | invalid | invalid | 95232 | 0 |

The error matrix clearly shows relations of errors and segments/couplers such that it can be used for automatic or manual error analysis.

Based on the content of the error or status matrix, the multiplexing of channels may be changed to avoid slow or defective combination of transmission line segments and receiving couplers.

In an embodiment, a controller is provided which is configured to evaluate the error or status matrix and to provide an error or status indication and/or to provide a reconfiguration of the transmit signal processor and/or receive signal processor based on the data field values.

Instead of error counts per time interval also an error rate might be displayed, e.g., $1.15 \cdot 10^{-3}$.

A method of status evaluation of a rotating capacitive data link system comprising a at least one transmission line with at least two transmission line segments connected to least two receiving couplers includes the steps of generating an error or status matrix comprising at least one data field for every usable combination of transmission line segments and receiving couplers, wherein the at least one data field (910) is configured to contain at least one of an error and/or status indication value. The method may be combined with any of the features disclosed herein. The method may further include steps for performing any of the features disclosed herein. The method may be applied to a system as disclosed herein.

The receive signal processor may be configured to perform live receiver-based diagnostics, which may be used for further general troubleshooting purposes. The following checks may result in receiver status signals as specified below:

Validity of encoded data: Encoded data validity may be signaled, when the received and coded data (e.g., 8b10b) is considered good. Such a signal may be given after minimal 8 us of reception without any code error. At this stage only the blocks of a line code used are analyzed.

Validity of frames: Frame validity may be signaled, when valid frames are received for a minimum time interval e.g., for at least 100 ms. At this stage only the frames are analyzed. A frame is a simple container for a single network packet and may include a plurality of data blocks.

The results either as counters or flags may be stored in the error or status matrix. If both signals are valid during standstill and/or rotation of the slipring all receivers may be operating correctly.

If one or both signals are invalid for at least one receiver during rotation the receiver is defective or not supplied with power or the receiving coupler connected to the receiver is incorrectly adjusted. For the case, the receivers are connected via optical fiber to a data switch the fault condition might also be a broken fiber or debris at one end of the fiber causing increased bit errors.

If one or both signals are invalid for exactly one receiver this can be the result of a standstill with one receiving coupler being located at a transmission line gap (mechanical gap) between two different transmission lines.

This diagnostic may be implemented for each receiver.

The receive signal processor may be configured to perform live user-channel based diagnostics. The following checks resulting in link status signals:

Validity of transmit frame rate: a valid transmit frame rate may be signaled, if the number of received frames per time unit is in a valid interval. The measured frame rate may be low pass filtered before comparing it with an upper limit value and/or a lower limit value.

Transmit loss rate: a rate of lost frames may be signaled, based on the counted lost frames during a specified time interval. The measured frame rate may be low pass filtered before comparing it with a limit value. A transmit loss may be signaled, if a transmission loss is detected, e.g., with defective transmitters or transmitters without power supply. For the case, the transmitters are connected via optical fibers to a data source the fault condition might also be a broken fiber or debris at one end of the fiber causing increased bit errors.

A good user channel signal may be signaled, if the frame rate is in a valid range and the transmit loss rate is below a predetermined limit value.

This diagnostic may be implemented for each user channel.

The receive signal processor may be configured to perform a frame gap analysis. During operation of the link, counter matrices are generated, counting frame losses and/or measuring frame gaps e.g., for each receiving coupler and/or each set of receiving couplers.

Snapshots of the frame gap counter matrices may be stored regularly to a system server logfile or database. This may be useful, if the receive signal processor does not contain non-volatile memory. Therefore, snapshots of the frame gap counters may need to be stored outside of the receive signal processor, e.g., on a system server within a logfile or a database. It may be recommended to store a new snapshot including timestamp every hour, but only in case of errors (if there is a difference in counter values). These stored snapshots can be post processed for analysis, including error localization including RX (receive)/TX (transmit) error separation, evaluation of error severity (no. of transmission gaps), and evaluation of trends, degradations (over time).

A gap in the received frame counter value (which are part of the frame header and are generated and inserted by the transmit signal processor if not included already) is clear evidence for lost frames (SR-Frame). When there is a gap in the continuous stream of frames, the respective frame loss counters and frame gap counters will increment accordingly. The frame losses and/or frame gap are counted in counter related to the transmitter and transmission line segment address or number and related to the receiver and receiving coupler address or number to be able to distinguish between an error condition caused by the transmit side (e.g., transmitter or transmission line or transmission line segment related) or by the receive side (e.g. receiving coupler, receiver related). By sorting/displaying these frame losses and/or frame gap counters in a matrix the error cause can be evaluated easily for debugging.

If the frame loss event occurs within a channel transition, the loss of a frame cannot always be clearly assigned to one receive channel. This is called ambiguous loss event. In case of an ambiguous loss event the counter value for both receiver channels involved (fade-out channel and fade-in channel) will be incremented. In the case of an ambiguous event the loss counter is increased per lost frame but the frame loss counter of both receivers is incremented. The frame loss counter and the gap counter of the transmitter is incremented.

The frame gap has a width/length determined by at least one of receiving coupler length, gap between the neighboring signal transmission lines, PLL settle time, rotation speed, and protocol frame length. This length is constant with only minor jitter. Only when there are distortions caused by e.g., a faulty PLL in the receiver, a misaligned receive antenna or transmit antenna, the length of the gap might deviate. The gaps of the received frame sequence can either be monitored in their start and end position and by its time or by an encoder position and drifts or deviation of position and width signaled to a service engineer.

The frame gap can be evaluated in relation to the rotational speed. It should decrease with increasing speed up to certain limit where the gap value is dominated by PLL settling time and frame length.

The frame gap can be displayed end evaluated in relation to the rotational angle—the gap position in an error free system is distributed directly correlated to its mechanical position. This results in an equally spaced distribution but may also be different if the angles are not identical but some of the receivers differ from the ideal position, e.g., because of mechanical reasons resulting from the structure of the system. Each of the receivers may have a PLL (phase locked loop) synchronizing the digital receiver to the received serial protocol. A clock may be recovered by the PLL evaluation the serial information transition which has a certain density guaranteed by the encoding which may be 8b10b or 64b66b.

The error or status matrix may contain error values and/or frame gap values and/or loss counters. It may also contain status information generated from these values. The values may be incremented until deleted or may be counted for a defined time interval generating an error rate or show varying effects (e.g., over time or at different speeds).

The error or status matrix might be displayed as a (Live=regularly updated) receiver-oriented diagnostics for general trouble shooting purpose or as Live user-channel-oriented diagnostics for general trouble shooting purpose, the user channel typically represented by the transmitters or transmission line segments.

In an embodiment, the transmission line segments completely encircle the first body, which may have a cylindrical shape. The number of transmission line segments may be different to the number of matching receiving couplers. This is especially useful, if the transmission line segments have the same length and the matching receiving couplers are spaced equally. As with the same number of segments and couplers, there is no signal coupling if all couplers are at the mechanical gaps between transmission line segments. With different numbers (if the numbers are not too high), only one coupler may be at a mechanical gap at one time. The other couplers may receive undistorted signals. The same result may be achieved by having transmission line segments of different lengths and/or by unequal spacing of receiving couplers.

Embodiments may include disc shaped arrangements with the transmission line segments being arranged and/or spaced axially or cylinder or drum shaped arrangements with the transmission line segments being arranged and/or spaced radially or a combination thereof.

An example of a protocol, herein called SR protocol, is described below:

Protocol Structure

|  | Bytes | Words |
|---|---|---|
| SR-Protocol: |  |  |
| Start of frame (SOF) | 4 | 0.5 |
| Scrambler seed (SCS) | 4 | 0.5 |
| Frame counter | 4 | 0.5 |
| Source address | 2 | 0.25 |
| Reserved | 2 | 0.25 |
| Payload TDATA | 1024 | 128 |
| Payload TUSER | 16 | 2 |
| Frame valid info | 16 | 2 |
| CRC | 8 | 1 |
| Inter packet gap | 8 | 1 |
| Summary: |  |  |
| SR-Protocol overhead | 16 | 2 |
| SR-Frame overhead | 32 | 4 |
| SR-Frame payload | 1040 | 130 |
| SR-Frame length | 1072 | 134 |
| Total packet length | 1088 | 136 |
| Total overhead | 48 | 6 |
| Protocol efficiency (%) | 95.58 |  |
| 8b10b efficiency (%) | 80 |  |
| Overall efficiency (%) | 76.47 |  |

The SR-Protocol generates a continuous stream of packets of constant size called SR-Frames.

Scrambling

The SR-Frame as example of a frame protocol definition uses data scrambling (polynomial: x31+x28+1) to reduce electro-magnetic interference. The whole SR-Frame as well as IPG (inter packet gap) are scrambled. The only unscrambled parts are the SR-Protocol's SOF and SCS fields. This leads to a flat spectrum with negligible influence of the unscrambled parts of the protocol.

Advanced Diagnostics may include three features as listed below:

| Diagnostics Feature | Resources | Purpose |
|---|---|---|
| Receiver status monitors | Implemented per receiver:<br>RX_8B10B_GOOD[0: C + R − 1]<br>8b10b valid signal<br>RX_FRAME_VALID[0: C + R − 1]<br>valid frames signal (CRC ok) | Live receiver-oriented diagnostics for general trouble shooting purpose |
| Link status monitors | Implemented per user-channel:<br>TX_VALID_RATE[0: C − 1][16 bits] filtered valid frames rate<br>TX_LOSS [0: C − 1]<br>concentrated frame loss signal | Live user-channel-oriented diagnostics for general trouble shooting purpose |
| Frame gap analysis | Frame loss counts<br>TX_LOSS_CNT[0: C − 1]<br>#RX * #TX * 64 bits<br>Frame gap matrix<br>FRAME_GAPS[0: C + R − 1, 0: C − 1]<br>FRAME_GAPS_AMB[0: C + R − 1, 0: C − 1]<br>#RX * #TX * 64 bits | Detailed failure matrices for field service support. |

FEC Secured Data Transmission

Data transmission could be secured by FEC (forward error correction). This feature is not yet implemented into the GigaCAP-HD IP cores. However, other GigaCAP products are equipped with such FEC and are in production and in the field since 2016.

The FEC would operate on SR protocol frames. Each frame would contain its own FEC information. One frame would be transmitted on one GigaCAP channel. No spreading of frames over several GigaCAP channels would be done. GigaCap and GigaCap HD refer to capacitive transmission line systems. GigaCap is a non-multiplexed transmission line system. GigaCap HD is a rotation dependent multiplexed transmission line system.

Here are some figures of how the FEC could perform:

| Algorithm | Reed-Solomon (255, 239, 8) (ITU G.709) |
|---|---|
| IP-Core | Xilinx Reed Solomon encoder and decoder |
| Correctable symbols | 8 per frame |
| Efficiency penalty | 4% (efficiency 76% → 72%) |
| Latency penalty | <5 µs |

BRIEF DESCRIPTION OF THE DRAWINGS

In the following the invention will be described by way of example, without limitation of the general inventive concept, on examples of embodiment with reference to the drawings.

FIG. 1 shows a basic concept of an embodiment

FIG. 4 shows a block diagram of an embodiment.

FIG. 8 shows an embodiment of a frame gap matrix.

DETAILED DESCRIPTION

Figure 2:
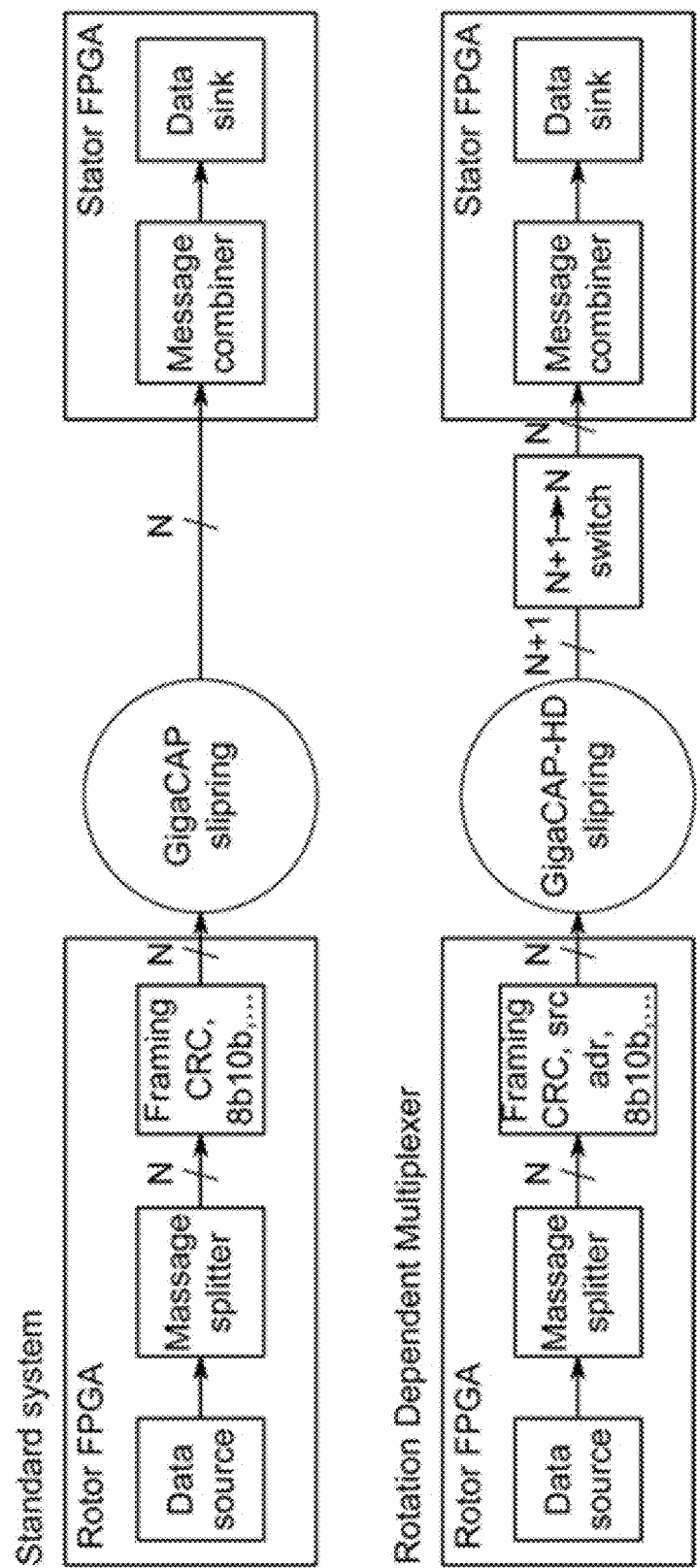
FIG. 2 shows rotation dependent multiplexer in comparison to a standard system.

FIG. 1 includes 2 sections or sub-figures: FIGS. 1a and 1b. It shows a basic concept of an embodiment of a rotating capacitive data link system 100 using position and thus rotation angle dependent multiplexing scheme is shown in the top section of the figure. A plurality (e.g., four) of such data links may be connected in parallel to increase throughput and reliability. Here only one such link is shown, connecting the first body 110 "Rotor" to the second body 120 "Stator" having one transmission line for transferring signals of two channels "a" and "b". Each channel may have at least one optoelectrical converter "OE" for converting optical to electrical signals and vice versa. At least one optoelectrical converter "OE" is driving a transmitter "Tx" 410.411 for each channel, further driving at least one circular shaped transmission line segment. There may be a higher number of channels, optoelectrical converters, transmitters, and transmission line segments.

The signal is received by receiving couplers, which are shown as short arc shaped segments. There may be one more receiving coupler 311, 312, 313 than the transmission line segments, in this case 3. The receiving couplers are connected to receivers "Rx" 510, 511, 512, further connected to at least one optoelectrical converter "OE". These are further connected to a switch which is reducing (demultiplexing) the number of lines, here from 3 to two output lines "a" and "b". As stated, multiple transmission lines can be stacked, in this case only one is shown.

Below is a diagram showing the different receive phases as the receivers mounted to the second body (stator) receive the signals sent by the rotating transmitters.

When a receiver is leaving one transmission line segment to cross over to the next transmission line segment, (case 1) a data frame might be cut off (b4), corrupt data might be received for some time (X) before a signal is received again (a5) but not a complete frame might be received (a5) or the frame header is not detected on the first frame.

The receive signal processor needs to assign streams by evaluating the received frames by reading the frame header. Also, lost or defective data may be counted.

Also, the receive signal processor might find double received frames and delete one to not increase total data rate by redundant information.

FIG. 1a shows the left side of FIG. 1 enlarged. FIG. 1b shows the right side of FIG. 1 enlarged.

FIG. 2 shows rotation dependent multiplexer in comparison to a standard system. In a standard capacitive link system one transmission line has only one segment, the transmission line segment is connected to one transmitter or multiple segments connected to the same transmitter. The receiving coupler connected to the receiver receives the signal transmitted during rotation, the transmission line is covering nearly 360 degrees. A plurality (N) of such data links may be connected in parallel to increase throughput.

In an embodiment according to the invention, each transmission line includes of multiple segments, each segment connected to a transmitter. At least one more (N+1) receiving couplers each with a receiver connected receiver and then transmitters (N) and transmission line segments are implemented. A receive signal processor deletes corrupt and double received frames.

If dimensioned correctly, the rotation dependent multiplexer system can transmit the same data rate in the volume of one transmission line as N standard systems.

In both system the protocol employs framing of the data (line encoding, header insertion with Checksum, source and/or receive address, frame counter, scrambling, etc), this framing can be part of the protocol anyway or additionally inserted by a transmit signal processor to optimize operation independent on the user specific or standardized protocol existing.

Figure 3:
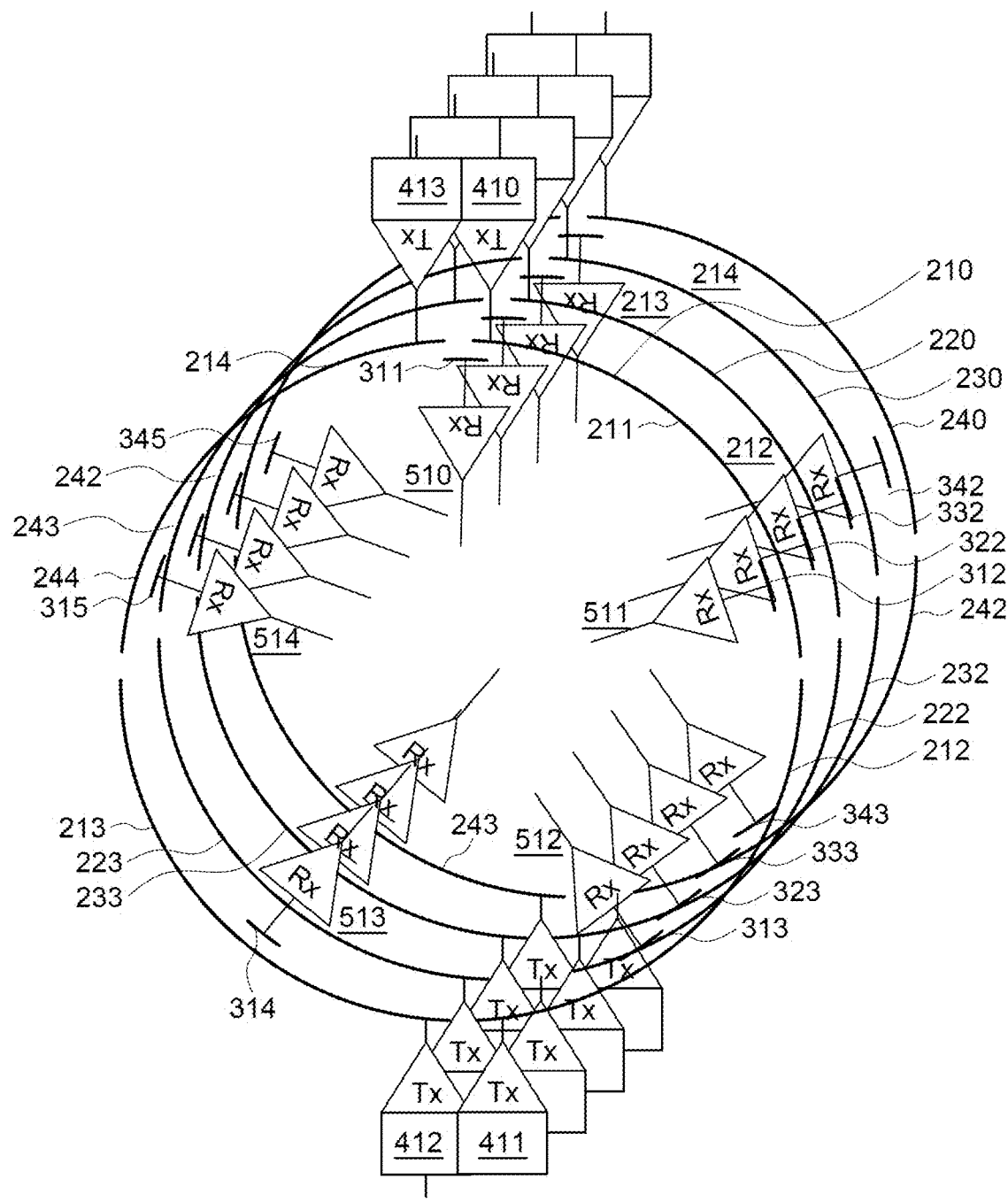
FIG. 3 shows a system with 4 rings and 4 sections per ring.

FIG. 3 shows a system with 4 rings and 4 sections per ring.

Each (circular) transmission line 210 includes at least 2 transmission line segments 211, 212, 213, 214 each connected to a transmitter, in this FIG. 4 four circular transmission lines 210, 220, 230, 240 are shown each having four transmission line segments. Each arc shaped transmission line segment is connected to a transmitter "Tx". The signal is received by receiving couplers 311, 312, 313, 315, shown as short arc shaped segments, the receiving couplers being one more than the transmission line segments. Each receiving coupler is connected to a receiver "Rx". Multiple circular transmission lines can be stacked, in this case four 210, 220, 230, 240.

FIG. 4 includes 3 sections or sub-figures: FIGS. 4a, 4b and 4c. FIG. 4 shows a block diagram of an embodiment. FIG. 4a shows part of the first body "Rotor Board" enlarged. FIG. 4b shows the "Slipring" ("GigaCAP-HD slipring") enlarged. FIG. 4c shows part of the second body "Stator Board" enlarged.

On the first body (rotor) the transmit signal processor 400 is shown with an interface "Rotor Interface" which may be part of a "Rotor FPGA", connected to the rotor devices generating the data (e.g. the detector in a CT scanner), the transmit signal processor ("Rotor-IP-core") employing framing of the data (line encoding, Header insertion with Checksum, source and/or receive address, frame counter, scrambling, etc.), this framing can be part of the protocol anyway or additionally inserted by the transmit signal processor to optimize operation independent on the user specific or standardized protocol existing. There may be optoelectrical converters, which may be according to the QSFP standard (Quad Small Form-factor Pluggable), or any other suitable type.

A rotation dependent multiplexer as described in FIG. 3 may be used for transmission. Furter, a system with 4 rings and 4 sections per ring as shown in FIG. 3 may be used to connect the first body with the second body.

One the second body (stator) the receive signal processor 500 is shown with an interface ("Stator interface") which may be part of a "Stator FPGA", connected to the stator devices evaluation the data (e.g., storage or reconstruction processor of a CT scanner), the receive signal processor ("Stator-IP-core") evaluating the framing of the data reconstructing or deleting corrupt information, deleting corrupt information and if required sorting or demultiplexing the data stream which were multiplexed to varying receivers by evaluating the address contained in the frame. The framing can be deleted if inserted only for the data transmission by the transmit signal processor.

Figure 5:
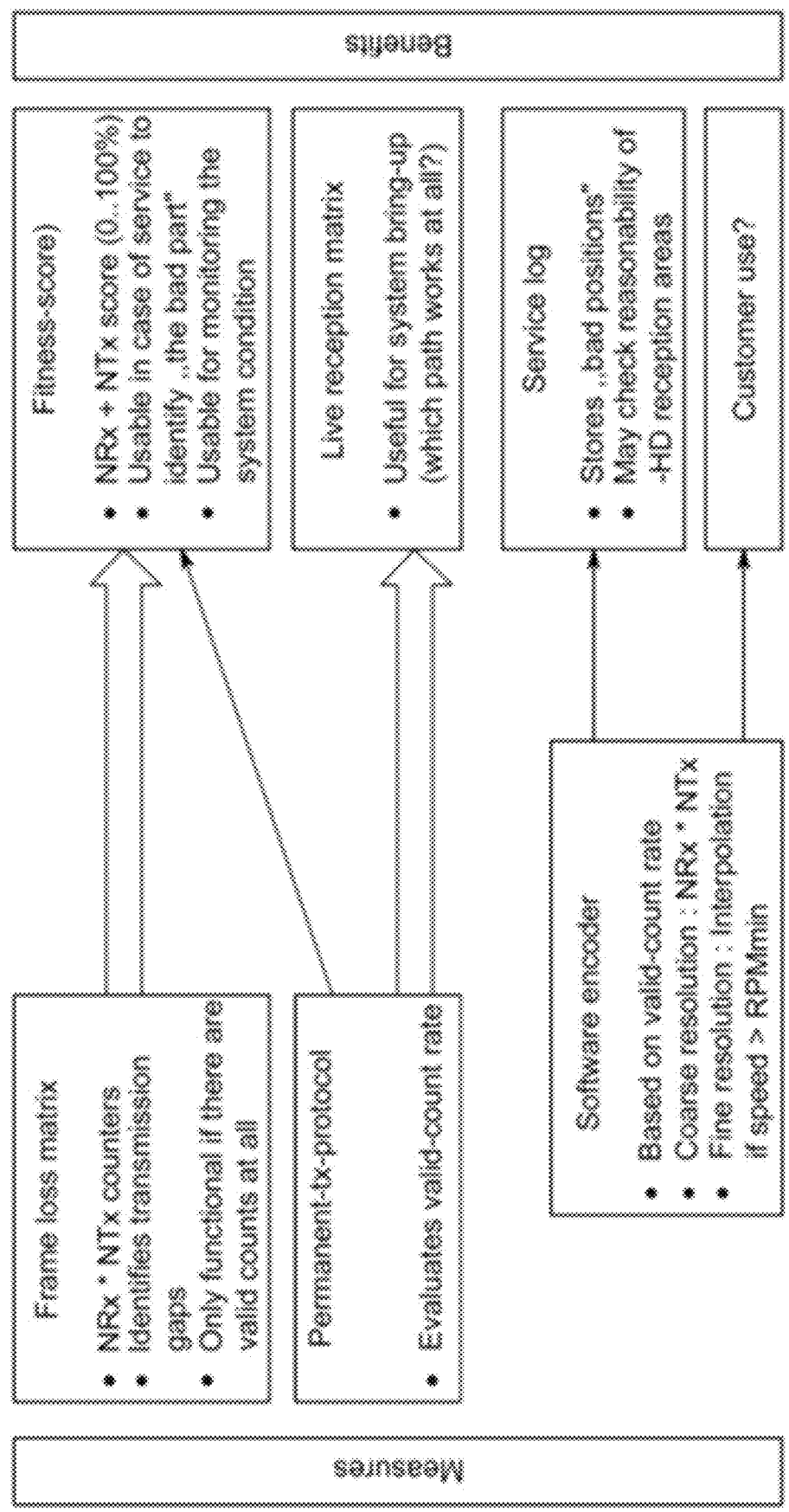
FIG. 5 shows advanced diagnosis measures and benefits.

FIG. 5 shows advanced diagnosis measures and benefits.

Measures: The frame losses and frame gaps can be sorted and displayed by transmitter and receiver as an error or status matrix. Thus, allowing to calculate a fitness level for each transmit and receive component, each transmission line.

Frame gaps can be counted per frame gap (incremented by one independent of the number of frames) and/or the width can be counted by counting the frames lost.

Transmitted frame counters ("NRx") and received frame counters ("NTx") may be used to build a frame loss matrix. This may also identify transmission gaps. This works only, if there are valid counts. There may be a permanent transmit control ("Permanent-tx-protocol") to evaluate a valid count rate. A software encoder may be based on valid-count rate and may provide with a coarse resolution NRx*NTx and a fine resolution by interpolation, e.g. if the rotation speed is less than a minimum speed (speed>RPMmin).

Benefits: It can be displayed live allowing fast and real time testing during assembly, fast evaluation of improvements, e.g., if receivers or connection cables or fibers are aligned or exchanged by factory or service persons.

A service log may evaluate trends or error cases that occur sporadically.

Status or error information might be compared to known cases to allow a service software to propose repair work actions or further tests.

A fitness score may show NRx+NTx scores (0 . . . 100%), which may be usable in case of service to identify "the bad part" or usable for monitoring the system condition. A live reception matrix may be useful for system bring-up to determine which path works at all?

Figure 6:
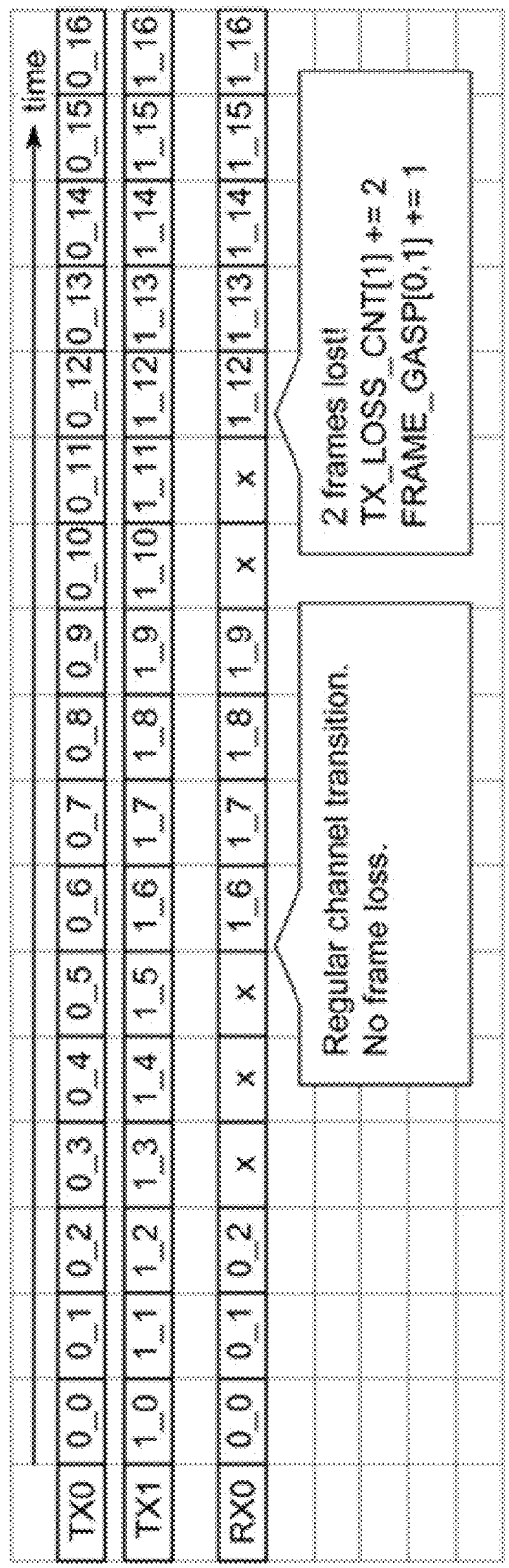
FIG. 6 shows the frame numbers of frames transmitted from two transmitters to one receiver.

FIG. 6 shows the frame numbers of frames transmitted from two transmitters (TX0, TX1) to one receiver (RX0). When there is a gap in the frame count sequence and the source address (TX channel) is different, then this is most likely a regular transition. No loss or gap counter will be incremented. When there is a gap in the frame count sequence and the source address stays the same, then certainly frames are lost. The loss or gap counters will be incremented, accordingly.

So, in the figure normal transition (marked green) is described first and an error condition (marked red) shortly afterwards.

The diagnosis for the receiver or receive channel detects a transition by evaluation of the source information in the frames. The receiver does not count losses, the frame gap counter of the receiver is incremented by 3 in total, so the losses can be detected.

in the error condition losses of the transmit channel are detected by the diagnosis by evaluating the consecutive frame counter of the frames.

Figure 7:
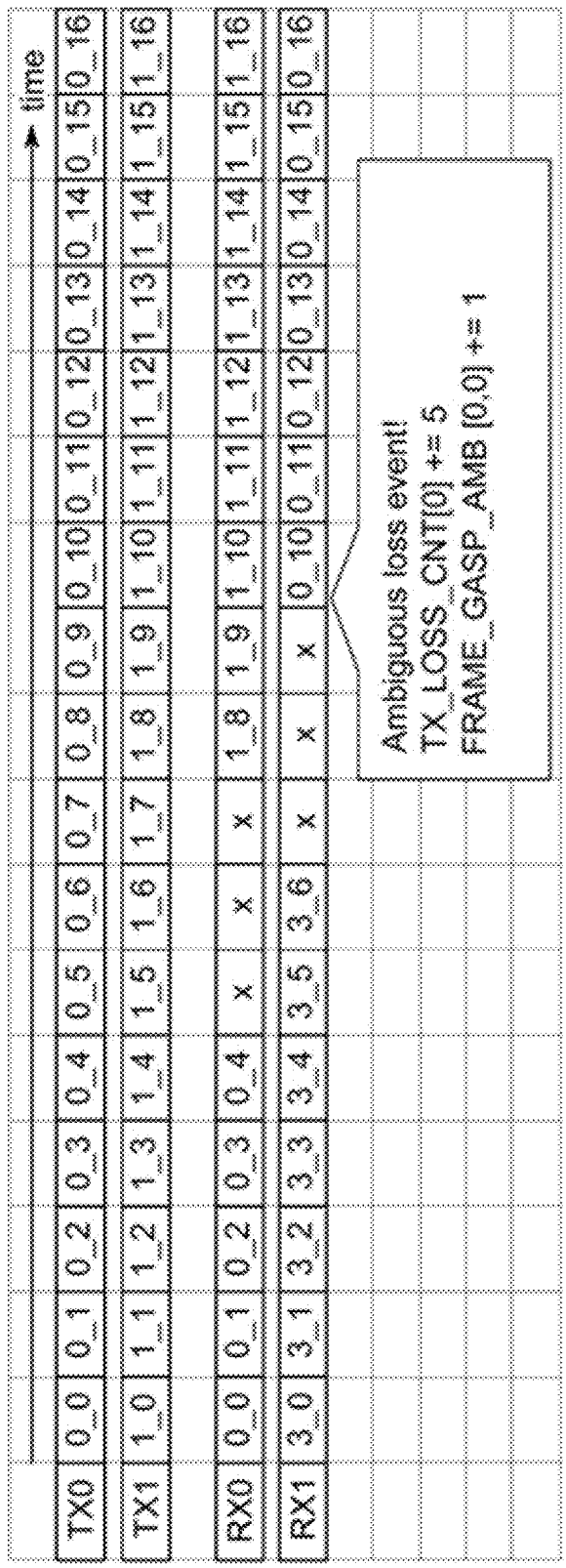
FIG. 7 shows the frame numbers of frames transmitted from two transmitters to two receivers.

FIG. 7 shows the frame numbers of frames transmitted from two transmitters (TX0, TX1) to two receivers (RX0, RX1). If the loss event occurs within a channel transition, the loss event cannot be clearly assigned to one receive channel. This is called ambiguous loss event. In case of an ambiguous loss event the frame gap counters of both receiver channels involved (fade-out channel and fade-in channel) will be incremented. The loss counter of the transmitter will only be incremented once. In this case there is one ambiguous frame detected, incrementing the ambiguous frame counter of the transmitter, increasing both of frame gap counters of the receiver involved, the frame gap width counters of both receivers are counted to 3, the transmit loss counter is incremented by 5. Thus, an error condition is described here since 5 frames are lost, this is not a normal operation condition but an error condition.

FIG. 8 shows an embodiment of a frame gap matrix, which may be part of a status matrix 900. The counters may be implemented as 64-bit counters. They may be seen as lifetime counters because there is a maximum of 1E6 frames per second (=20 bits) and 3E13 frames per year (=37 bits). Nevertheless, counters may clip at 0xFFFFFFFFFFFFFFFF to avoid wraparounds. It may be recommended to reset the frame gap counters only at power-up after the system has entered a known-good state.

To analyze the exact frame gap width, the RX data valid signal was read out via angle position (encoder in Gantry setup). The RX data valid signal is 1 if no frame error is present.

The frame gap width, the frame gap angle in relation to the rotation may be evaluated. The frame gap angle might be calculated with the help of a timer counter or by reading an encoder value.

The frame gap might be evaluated dependent on the rotational speed, the frame gap and receive margin might be displayed per each receiver. The receive margin being the difference between actual frame gap and a defined threshold value or max. frame gap, the max. frame gap being the longest gap that can be tolerated without having frame losses, that means no frames are lost because always at least one receiver is synchronized on the data stream and receives a valid signal containing at least a full frame.

Figure 9:
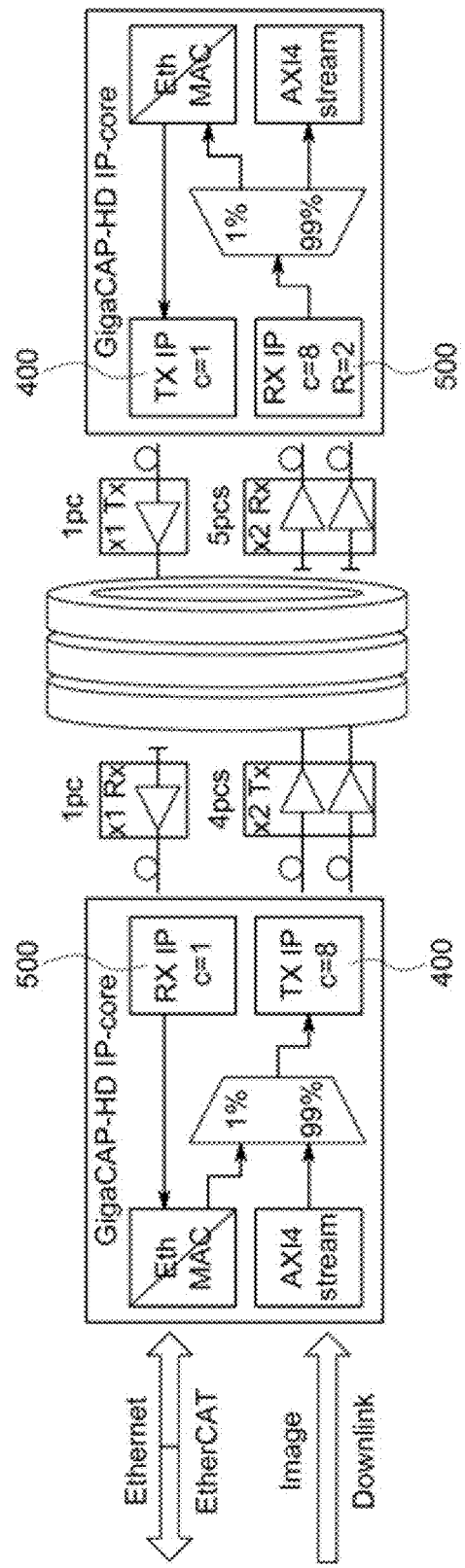
FIG. 9 shows a block diagram of another embodiment.

FIG. 9 shows a block diagram of another embodiment.

On the first body (left side) and on the second body (right side) a receive signal processor 500 ("RX IP") and a transmit signal processor 400 ("TX IP") are shown plus a transceiver signal processor.

The downlink (left to right direction) is including a multiplexed capacitive transmission link having 2 transmission lines with 4 segments each, the uplink of a standard capacitive transmission link having one transmission line with one transmission line segment. Uplink and downlink each are unidirectional but can be combined to form a bidirectional link as shown here.

In this case an image data link for the downlink is shown with high data rate and a lower data rate bidirectional control bus is multiplexed into the downlink in one direction, for the uplink a standard capacitive transmission link is used in this example.

Diagnostics can be implemented on each of the signal processors, the values may be distributed via the bidirectional bus to a service computer connected to the stationary side of the system, e.g., the second body via the control bus.

The number of parts is designated by the postfix ("pc" or "pcs") for piece or pieces. Ethernet and EtherCAT are industrial communication/network standards. Eth MAC stands for ethernet MAC (Medium Access Control). AXI4 is an interface standard (Advanced extensible Interface).

LIST OF REFERENCE NUMERALS 100 rotating capacitive data link system
110 first body
120 second body
130 rotation axis
150 uplink
151 uplink receiver
152 uplink transmitter
160 controller
210 first circular transmission line
211-214 first transmission line segments
220 second circular transmission line
221-224 second transmission line segments
230 third circular transmission line
231-234 third transmission line segments 240 forth circular transmission line
241-244 forth transmission line segments
310 first circular set of receiving couplers
311-315 first receiving couplers
320 second circular set of receiving couplers
321-325 second receiving couplers
330 third circular set of receiving couplers
331-335 third receiving couplers
340 fourth circular set of receiving couplers
341-345 fourth receiving couplers
400 transmit signal processor
410-413 transmitter
500 receive signal processor
510-514 receiver
900 error or status matrix
910 data field

The invention claimed is:

1. A rotating capacitive data link system comprising:
a first body and a second body, the first body being rotatable relative to a second body around a rotation axis,
the first body including one or more circular signal transmission lines, wherein and each of the one or more circular signal transmission line includes at least two transmission line segments, with at least one mechanical gap between the at least two transmission line segments,
the second body including one or more circularly arranged sets of receiving couplers, wherein each of the one or more circularly arranged sets of receiving couplers comprises at least two receiving couplers arranged circumferentially around the rotation axis,
wherein:
each of the one or more circularly arranged sets of receiving couplers is capacitively coupled to one of the one or more circular signal transmission lines such that, depending on a relative rotational position or angle between the first body and the second body, there exist multiple capacitively coupled paths between the at least two transmission line segments of said each of the one or more circular signal transmission lines and at least two receiving couplers arranged circumferentially around a rotation axis of a matching set of the at least one circularly arranged set of receiving couplers, and
each of the at least two receiving couplers is connected to a receive signal processor at the second body,
wherein:
the receive signal processor is further configured to provide at least one error or status matrix that comprises at least one data field for every combination of the at least two transmission line segments and the at least two receiving couplers of each of the one or more circular signal transmission lines with a corresponding matching set of the at least one circularly arranged set of receiving couplers, wherein the at least one data field is configured to contain at least one of an error value and a status indication value.

2. A data link system according to claim 1,
wherein the receive signal processor is configured to provide the at least one error or status matrix in real-time.

3. A data link system according to claim 1, wherein each of the at least two transmission line segments is connected to a transmit signal processor of the first body, wherein the transmit signal processor of the first body is configured to repackage a protocol by adding at least one of: a frame counter value, a source address, and a transmit channel address and/or wherein the transmit signal processor of the first body is configured to scramble the protocol.

4. A data link system according to claim 3,
further comprising a controller configured to evaluate the error or status matrix and to provide an error or status indication and to provide a reconfiguration of the transmit signal processor and/or receive signal processor based on values of the at least one data field.

5. A data link system according to claim 4, wherein the controller is configured to collect error or status information of the receive signal processor and the transmit signal processor and/or a transceive signal processor combining the transmit signal processor and the receive signal processor, the controller configured to communicate with at least one of said receive signal processor and transmit signal processor and/or transceiver signal processor via a multiplexed and/or unmultiplexed capacitive link system.

6. A data link system according to claim 3,
wherein the transmit signal processor is configured to translate at least one data stream of a user channel into at least one of a plurality of parallel data streams that are transferred over the multiple capacitively coupled paths, and wherein the receive signal processor is configured to assemble the plurality of parallel data streams back to the at least one data stream of the user channel.

7. A data link system according to claim 1,
wherein the at least one error or status matrix comprises
(i) a row for every transmission line segment of the at least two transmission line segments and a column for every receiving coupler of the at least two receiving couplers, or
(ii) a column for every transmission line segment of the at least two transmission line segments and a row for every receiving coupler of the at least two receiving couplers.

8. A data link system according to claim 1, further comprising a controller configured to store an error or status indication in defined time intervals or after changes of the at least one of the error value and the status indication value.

9. A data link system according to claim 8,
wherein a transceive signal processor of the first body comprises a unidirectional user channel of a corresponding receive signal processor and a unidirectional user channel of a corresponding transmit signal processor,
wherein said transceive signal processor of the first body is configured to aggregate a respective bidirectional bus signal combining a corresponding uplink user channel and a corresponding downlink user channel,
and
wherein a transceive signal processor of the second body comprises a unidirectional user channel of a corresponding receive signal processor and a unidirectional user channel of a corresponding transmit signal processor,
wherein said transceive signal processor of the second body is configured to aggregate a respective bidirectional bus signal combining a corresponding uplink user channel and a corresponding downlink user channel.

10. A data link system according to claim 9, wherein a transmit signal processor of a transmit signal processor of the first body and a transmit signal processor of the second body comprises individual transmitters that are connected to each of the at least two transmission line segments, and a receive signal processor of a receive signal processor of the first body and a receive signal processor of the second body comprises individual receivers that are connected to each of the at least two receiving couplers.

11. A data link system according to claim 1, wherein the first body further comprises an uplink receiver matching to an uplink transmitter of the second body and configured to transfer data from the second body to the first body.

12. A data link system according to claim 1, wherein an error or status matrix for uplink and an error or status matrix for downlink are separate matrices or united in one multidimensional matrix.

* * * * *